United States Patent [19]
Schadt et al.

[11] Patent Number: 5,322,638
[45] Date of Patent: Jun. 21, 1994

[54] HALOPHENYL SUBSTITUTED DIOXANES

[75] Inventors: Martin Schadt, Seltisberg; Alois Villiger, Basel, both of Switzerland

[73] Assignee: Hoffmann-La Roche Inc., Nutley, N.J.

[21] Appl. No.: 858,447

[22] Filed: Mar. 26, 1992

Related U.S. Application Data

[63] Continuation of Ser. No. 620,877, Dec. 3, 1990, abandoned.

[30] Foreign Application Priority Data

Dec. 19, 1989 [CH] Switzerland .......... 4539/89

[51] Int. Cl.$^5$ .......... C09K 19/34; C09K 19/12; C07D 319/06; G02F 1/13
[52] U.S. Cl. .......... 252/299.61; 252/299.66; 549/369; 359/103
[58] Field of Search .......... 252/299.61, 299.66; 549/369; 359/103

[56] References Cited

U.S. PATENT DOCUMENTS

| | | | |
|---|---|---|---|
| 4,323,473 | 4/1982 | Sethofer .......... | 252/299.61 |
| 4,486,332 | 12/1984 | Demus et al. .......... | 252/299.61 |
| 4,565,425 | 1/1986 | Petrzilka et al. .......... | 359/103 X |
| 4,629,581 | 12/1986 | Petrzilka et al. .......... | 252/299.63 |
| 4,676,604 | 6/1987 | Petrzilka .......... | 350/350 R |
| 4,702,562 | 10/1987 | Scheuble et al. .......... | 350/350 R |
| 4,704,227 | 11/1987 | Krause et al. .......... | 252/299.61 |
| 4,709,030 | 11/1987 | Petrzilka et al. .......... | 544/242 |
| 4,726,911 | 2/1988 | Krause et al. .......... | 252/299.61 |
| 4,755,323 | 7/1988 | Eidenschink et al. .......... | 252/299.61 |
| 4,886,621 | 12/1989 | Sage et al. .......... | 252/299.61 |
| 4,915,480 | 4/1990 | Petrzilka et al. .......... | 350/350 R |
| 5,100,577 | 3/1992 | Buchecker et al. .......... | 252/299.01 |
| 5,104,569 | 4/1992 | Leenhouts et al. .......... | 252/299.61 |
| 5,160,661 | 11/1992 | Schadt et al. .......... | 252/299.61 |
| 5,174,921 | 12/1992 | Bucheeker et al. .......... | 252/299.63 |
| 5,185,098 | 2/1993 | Buchecker et al. .......... | 252/299.63 |

FOREIGN PATENT DOCUMENTS

| | | |
|---|---|---|
| 122389 | 10/1984 | European Pat. Off. . |
| 168683 | 1/1986 | European Pat. Off. . |
| 269963 | 6/1988 | European Pat. Off. . |
| 315014 | 5/1989 | European Pat. Off. . |

OTHER PUBLICATIONS

Schadt et al., Liquid Crystal, vol. 7, No. 4, 519-536 (1990).

Primary Examiner—Robert L. Stoll
Assistant Examiner—C. Harris
Attorney, Agent, or Firm—George M. Gould; George W. Johnston; Robert A. Silverman

[57] ABSTRACT

Compounds of the formula

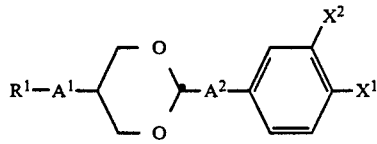

wherein $A^1$ denotes a single covalent bond and $A^2$ denotes 1,4-phenylene or trans-1,4-cyclohexylene or $A^1$ denotes trans-1,4-cyclohexylene and $A^2$ denotes a single covalent bond; $X^1$ signifies fluorine or chlorine; $X^2$ represents fluorine or, when $X^1$ signifies chlorine, also hydrogen or chlorine; and $R^1$ signifies 1E-alkenyl with 2 to 12 carbon atoms, their manufacture, liquid crystalline mixtures which contain such compounds and their use for electro-optical purposes.

10 Claims, No Drawings

HALOPHENYL SUBSTITUTED DIOXANES

This application is a continuation of application Ser. No. 07/620,877, filed Dec. 3, 1990, abandoned.

BACKGROUND OF THE INVENTION

1. Field of the Invention

The present invention is concerned with novel halophenyl-substituted dioxanes, their manufacture, liquid crystalline mixtures which contain these compounds as well as their use for electro-optical purposes.

2. Description of the Invention

Liquid crystals are used primarily as dielectrics in indicating devices, since the optical properties of such substances can be influenced by an applied voltage. Electro-optical devices based on liquid crystals are well-known to a person skilled in the art and can be based on various effects. Examples of such devices are cells having dynamic scattering, DAP cells (deformation of aligned phases), guest/host cells, TN cells having a "twisted nematic" structure, STN cells ("super-twisted nematic"), SBE cells ("super birefringence effect") and OMI cells ("optical mode interference"). The most common indicating devices are based on the Schadt-Helfrich effect and have a twisted nematic structure.

The liquid crystal materials must have a good chemical and thermal stability and a good stability towards electric fields and electromagnetic radiation. Further, the liquid crystal materials should have low viscosity and in the cells should give short response times, low threshold potentials and a high contrast. Further, at the usual operating temperatures of about −30° C. to about +80° C., especially of about −20° C. to about +60° C., they should have a suitable mesophase, for example a nematic or cholesteric mesophase for the above-mentioned cells. Further properties such as the electrical conductivity, the dielectric anisotropy and the optical anisotropy must fulfill different requirements depending on the type of cell and field of application. For example, materials for cells having a twisted nematic structure should have a positive dielectric anisotropy and an electrical conductivity which is as low as possible. For some years there has been a particular interest in actively addressed liquid crystal displays, e.g. TFT applications ("thin film transistor") in television sets. However, the use of cyano compounds having a positive dielectric anisotropy in such displays generally leads mainly to an undesired high increase in current.

Since liquid crystals are usually used as mixtures of several components, it is important that the components have a good miscibility with one another.

SUMMARY OF THE INVENTION

The present invention provides liquid crystalline compounds of the formula

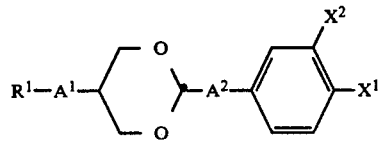

wherein $A^1$ is a single covalent bond and $A^2$ is 1,4-phenylene or trans-1,4-cyclohexylene or $A^1$ is trans-1,4-cyclohexylene and $A^2$ is a single covalent bond; $X^1$ is fluorine or chlorine; $X^2$ is fluorine or, when $X^1$ is chlorine, $X^2$ also can be hydrogen or chlorine; and $R^1$ is 1E-alkenyl with 2 to 12 carbon atoms.

The compounds in accordance with the invention are liquid crystals with high clearing points. Moreover, highly ordered smectic phases are completely or largely suppressed. They have surprisingly low viscosities, especially low rotation viscosities, and have a good miscibility with usual liquid crystal materials. In spite of the relatively weak permanent dipole moments, they have remarkably large positive dielectric anisotropies. In this respect they are to some extent even comparable with bicyclic cyano compounds, which, however, have low clearing points and high viscosities and in TFT applications lead to conductivity problems. The compounds in accordance with the invention therefore facilitate low threshold potentials and at the same time short switching times.

The compounds in accordance with the invention are especially suitable as components of nematic and cholesteric mixtures and, by virtue of their good solubility in one another and in known liquid crystals, can also be used in comparatively high concentrations.

DETAILED DESCRIPTION OF THE INVENTION

The present invention provides compounds of the general formula

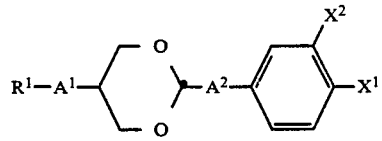

wherein $A^1$ is a single covalent bond and $A^2$ is 1,4-phenylene or trans-1,4-cyclohexylene or $A^1$ is trans-1,4-cyclohexylene and $A^2$ is a single covalent bond; $X^1$ is fluorine or chlorine; $X^2$ is fluorine or, when $X^1$ is chlorine, $X^2$ also can be hydrogen or chlorine; and $R^1$ is 1E-alkenyl with 2 to 12 carbon atoms.

The compounds in accordance with the invention are liquid crystals with high clearing points. Moreover, highly ordered smectic phases are completely or largely suppressed. They have surprisingly low viscosities, especially low rotation viscosities, and have a good miscibility with usual liquid crystal materials. In spite of the relatively weak permanent dipole moments, they have remarkably large positive dielectric anisotropies. In this respect, they are to some extent even comparable with bicyclic cyano compounds, which, however, have low clearing points and high viscosities and in TFT applications lead to conductivity problems. The compounds in accordance with the invention therefore facilitate low threshold potentials and at the same time, short switching times.

The compounds in accordance with the invention are especially suitable as components of nematic and cholesteric mixtures and, by virtue of their good solubility in one another and in known liquid crystals, can also be used in comparatively high concentrations.

The properties can be varied to a certain extent depending on the significance of the groups. A cyclohexane ring in $A^1$ or $A^2$ leads to comparatively low optical anisotropy. A benzene ring in $A^2$ leads to comparatively high optical anisotropy. Difluoro derivatives ($X^1=X^2=F$) give especially large dielectric anisotropies and comparatively short switching times. p-Chloro derivatives ($X^1=Cl$) usually give high clearing points and similarly short switching times.

The term "1E-alkenyl" embraces straight-chain and branched, optionally chiral, alkenyl residues. The straight-chain residues, such as vinyl, 1E-propenyl, 1E-butenyl, 1E-pentenyl, 1E-hexenyl, 1E-heptenyl, 1E-octenyl, 1E-nonenyl, 1E-decenyl, 1E-undecenyl and 1E-dodencenyl, are generally preferred.

Formula I embraces the compounds of the formulae

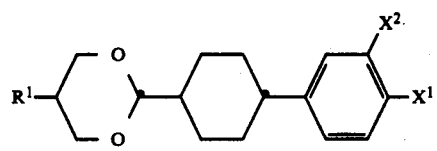

IA

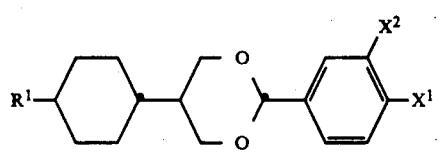

IB

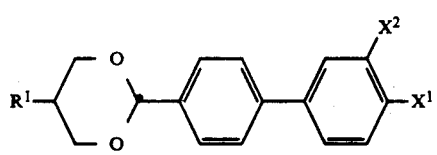

IC wherein $R^1$, $X^1$ and $X^2$ have the above significances.

Of the compounds of formulae I, IA, IB and IC above there are generally preferred those in which $X^1$ and $X^2$ signify fluorine when a large dielectric anisotropy is desired and those in which $X^1$ signifies chlorine and $X^2$ signifies hydrogen when comparatively high clearing points are desired.

Preferred residues $R^1$ are those with 2 to 7 carbon atoms, especially those with 2 to 5 carbon atoms.

The compounds of formula I can be manufactured in accordance with the invention by reacting an aldehyde of the formula

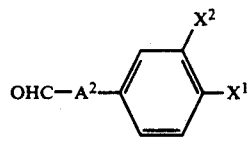

II or an acetal thereof with a compound of the formula

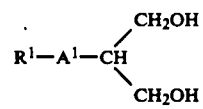

III wherein $R^1$, $A^1$, $A^2$, $X^1$ and $X^2$ have the above significances.

The reaction of the aldehyde of formula II or of a suitable acetal (e.g. the dimethyl acetal or ethylene acetal) with the diol of formula III can be effected in a manner known per se. Preferably, the reaction is effected in an inert organic solvent (for example, an aromatic hydrocarbon such as benzene, toluene or xylene) in the presence of a catalytic amount of an organic or inorganic acid such as p-toluenesulphonic acid, sulphuric acid or dry hydrogen chloride. Temperature and pressure are not critical. However, the reaction is preferably carried out at atmospheric pressure and reflux temperature with the separation of the water which is formed.

The starting materials of formulae II and III are known or are analogues of known compounds and can be prepared according to known methods. Suitable methods are illustrated in the Synthesis Examples.

The compounds of formula I can be used in the form of mixtures with one another and/or with other liquid crystal components, such as e.g. with substances from the classes of Schiff's bases, azobenzenes, azoxybenzenes, phenylbenzoates, cyclohexanecarboxylic acid phenyl esters, cyclohexanecarboxylic acid cyclohexyl esters, biphenyls, phenylcyclohexanes, cyclohexylcyclohexanes, phenylpyrimidines, cyclohexylpyrimidines, phenyldioxanes, 2-cyclohexyl-1-phenylethanes, terphenyls, cyclohexylbiphenyls, cyclohexylphenylpyrimidines and the like. Such substances are known to a person skilled in the art and many of them are, moreover, commercially available.

The liquid crystalline mixtures in accordance with the invention contain at least two components, of which at least one component is a compound of formula I. A second component and, if desired, further components can be additional compounds of formula I or other liquid crystal components. The compounds of formula I are especially suitable for nematic mixtures or, insofar as at least one component of the mixture is optically active, also for cholesteric mixtures.

Having regard to the good solubility of the compounds of formula I and having regard to their good miscibility with one another, the amount of these compounds in the mixtures in accordance with the invention can be relatively high. In general, however, an amount of about 1–50 wt. %, especially about 5–30 wt. %, of compounds of formula I is preferred.

The mixtures in accordance with the invention preferably contain, in addition to one or more compounds of formula I, one or more compounds from the group of compounds of the formula

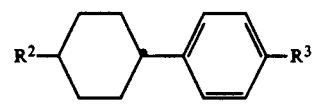

IV

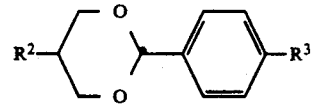

V

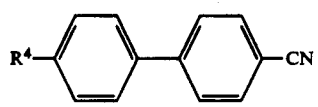

VI

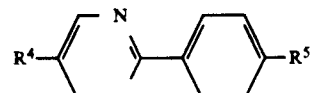

VII

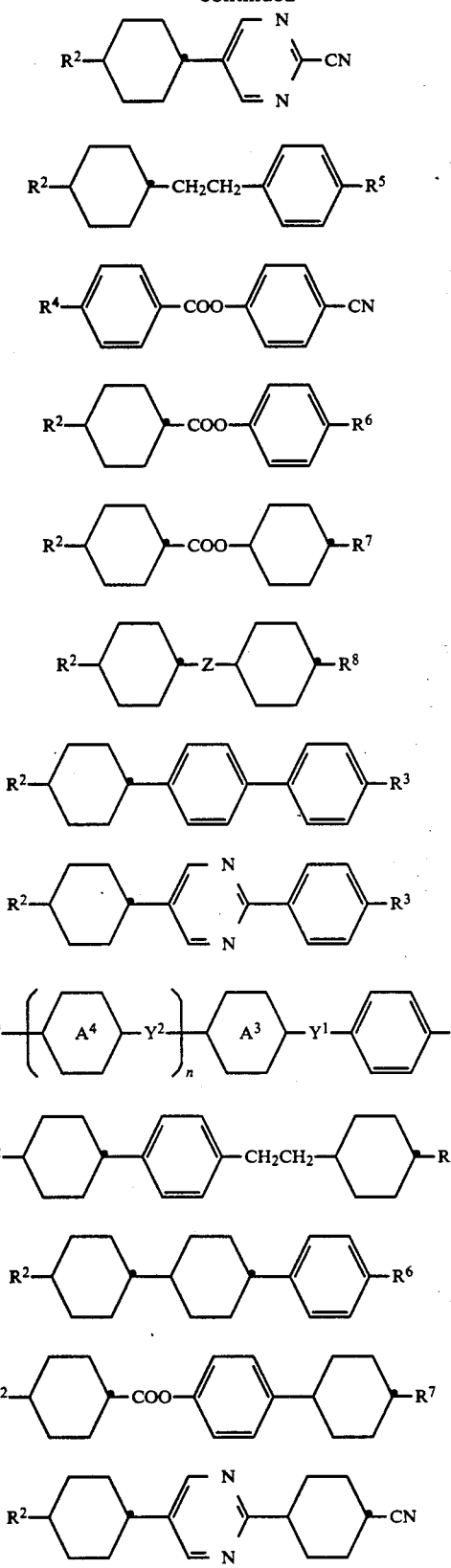

wherein $R^2$ and $R^7$ signify alkyl, 1E-alkenyl, 3E-alkenyl or 4-alkenyl; $R^3$ signifies cyano, —NCS, alkyl, 1E-alkenyl, 3E-alkenyl, 4-alkenyl, alkoxy, 2E-alkenyloxy or 3-alkenyloxy; $R^4$ signifies alkyl, 3E-alkenyl or 4-alkenyl; $R^5$ signifies cyano, —NCS, alkyl, 3E-alkenyl, 4-alkenyl, alkoxy, 2E-alkenyloxy or 3-alkenyloxy; $R^6$ signifies cyano, alkyl, 3E-alkenyl, 4-alkenyl, alkoxy, 2E-alkenyloxy or 3-alkenyloxy; Z signifies a single covalent bond or —CH$_2$CH$_2$—; $R^8$ signifies cyano, alkoxy, 2E-alkenyloxy, 3-alkenyloxy, alkyl, 1E-alkenyl, 3E-alkenyl, 4-alkenyl, alkoxymethyl or 2-alkenyloxymethyl; n stands for the number 0 or 1, one of the groups $Y^1$ and $Y^2$ signifies a single covalent bond, —COO—, —OOC—, —CH$_2$CH$_2$—, —CH$_2$O— or —OCH$_2$— and the other of the groups $Y^1$ and $Y^2$ signifies a single covalent bond; rings $A^3$ and $A^4$ each independently represent substituted or unsubstituted trans-1,4-cyclohexylene in which optionally 2 non-adjacent CH$_2$ groups are replaced by oxygen or substituted or unsubstituted 1,4-phenylene in which optionally 1 CH group or 2 CH groups is/are replaced by nitrogen; $R^9$ denotes alkyl, 1E-alkenyl or, when one of the groups $Y^1$ and $Y^2$ signifies a single covalent —COO—, —OOC— or —CH$_2$CH$_2$— and the other of the groups $Y^1$ and $Y^2$ signifies a single covalent bond, also 3E-alkenyl.

The alkyl, alkenyl, alkoxy and alkenyloxy residues $R^2$–$R^9$ in formulae IV–XX are preferably straight-chain residues. They preferably have up to 12, particularly up to 7, carbon atoms.

The mixtures in accordance with the invention can also contain optically active compounds (e.g. optically active 4'-alkyl- or 4'-alkoxy-4-biphenylcarbonitriles) and/or dichroic colouring substances (e.g. azo, azoxy or anthraquinone colouring substances). The amount of such compounds is determined by the solubility, the desired pitch, colour, extinction and the like. In general, the amount of optically active compounds and dichroic colouring substances amounts to a maximum of in each case about 10 wt. % in the total mixture.

The manufacture of the mixtures in accordance with the invention and the manufacture of the electro-optical devices can be effected in a manner known per se.

The manufacture of the compounds of formula I as well as liquid crystalline mixtures containing these compounds are illustrated in more detail by the following Examples. C signifies a crystalline phase, $S_A$ signifies a smectic A phase, $S_B$ signifies a smectic B phase, N signifies a nematic phase and I signifies an isotropic phase. $V_{10}$ and $V_{50}$ denote the voltage for 10% and, respectively, 50% transmission, $t_{on}$ and $t_{off}$ denote the switching-on time and, respectively, the switching-off time and Δn denotes the optical anisotropy. $k_{11}$ and $k_{33}$ signify the elastic constants for splaying and, respectively, bending. Δε denotes the dielectric anisotropy, η denotes the bulk viscosity and $γ_1$ denotes the rotation viscosity. The electro-optical properties were measured at 22° C. or at a temperature 10° C. below the clearing point. Unless indicated otherwise, the measurement was effected at 22° C. Unless indicated otherwise (such as by the use of present tense verbs), the Examples were carried out as written.

EXAMPLE 1

A solution of 3.0 g of trans-4-(3,4-difluorophenyl)cyclohexanecarboxaldehyde (prepared in accordance with Example 2) and 2.4 g of 2-(1E-propenyl)-1,3-propanediol in 75 ml of toluene was treated with 3 drops of 10 percent (v/v) sulphuric acid and the reaction mixture was heated to boiling for 1.25 hours, whereby moist toluene was distilled off and replaced by fresh toluene. Then, the reaction mixture was neutralized with triethylamine and, after cooling, washed three times with water, dried over sodium sulphate and concentrated. Chromatographic purification of the residue on 100 g of silica gel with hexane/ethyl acetate (vol. 49:1) and repeated recrystallization of the trans/cis mixture from hexane gave 0.8 g of pure trans-5-(1E-propenyl)-2-[trans-4-(3,4-difluoro-phenyl)cyclohexyl]-1,3-dioxane; m.p. (C-N) 96.0° C., cl.p. (N-I) 125.5° C., Δε (115° C.)=12.4.

The following compounds can be manufactured in an analogous manner:

trans-5-vinyl-2-[trans-4-(3,4-difluorophenyl)cyclohexyl]-1,3-dioxane;

trans-5-(1E-butenyl)-2-[trans-4-(3,4-difluorophenyl)cyclohexyl]-1,3-dioxane, m.p. (C-S$_B$) 42.7° C., S$_B$-N 79.5° C., cl.p. (N-I) 117.6° C.;

trans-5-(1E-pentenyl)-2-[trans-4-(3,4-difluorophenyl)cyclohexyl]-1,3-dioxane, m.p. (C-S$_B$) 68.8° C., S$_B$-N 81.0° C., cl.p. (N-I) 116° C.;

trans-5-(1E-heptenyl)-2-[trans-4-(3,4-difluorophenyl)cyclohexyl]-1,3-dioxane;

trans-5-vinyl-2-[trans-4-(4-chlorophenyl)cyclohexyl]-1,3-dioxane;

trans-5-(1E-propenyl)-2-[trans-4-(4-chlorophenyl)cyclohexyl]-1,3-dioxane, m.p. (C-N) 101° C., cl.p. (N-I) 183° C.;

trans-5-(1E-butenyl)-2-[trans-4-(4-chlorophenyl)cyclohexyl]-1,3-dioxane;

trans-5-(1E-pentenyl)-2-[trans-4-(4-chlorophenyl)cyclohexyl]-1,3-dioxane, m.p. (C-S$_B$) 102.4° C., S$_B$-N 117° C., cl.p. (N-I) 172.5° C.;

trans-5-(1E-propenyl)-2-[trans-4-(4-chloro-3-fluorophenyl)cyclohexyl]-1,3-dioxane, m.p. (C-N) 81.9° C., cl.p. (N-I) 141.5° C.;

trans-5-(1E-pentenyl)-2-[trans-4-(4-chloro-3-fluorophenyl)cyclohexyl]-1,3-dioxane, m.p. (C-N) 90.4° C., S$_B$-N 78.7° C., cl.p. (N-I) 139.5° C.;

trans-5-(1E-propenyl)-2-[trans-4-(3,4-dichlorophenyl)cyclohexyl]-1,3-dioxane;

trans-5-vinyl-2-(3',4'-difluoro-4-biphenylyl)-1,3-dioxane;

trans-5-(1E-propenyl)-2-(3',4'-difluoro-4-biphenylyl)-1,3-dioxane, m.p. (C-N) 106.9° C., cl.p. (N-I) 148.5° C.;

trans-5-(1E-butenyl)-2-(3',4'-difluoro-4-biphenylyl)-1,3-dioxane, m.p. (C-S$_A$) 104.6° C., S$_A$-N 131.5° C., cl.p. (N-I) 145° C.;

trans-5-(1E-pentenyl)-2-(3',4'-difluoro-4-biphenylyl)-1,3-dioxane, m.p. (C-S$_A$) 79.6° C., S$_A$-N 137.5° C., cl.p. (N-I) 148.5° C.;

trans-5-(1E-heptenyl)-2-(3',4'-difluoro-4-biphenylyl)-1,3-dioxane;

trans-5-vinyl-2-(4'-chloro-4-biphenylyl)-1,3-dioxane;

trans-5-(1E-propenyl)-2-(4'-chloro-4-biphenylyl)-1,3-dioxane;

trans-5-(1E-butenyl)-2-(4'-chloro-4-biphenylyl)-1,3-dioxane;

trans-5-(1E-pentenyl)-2-(4'-chloro-4-biphenylyl)-1,3-dioxane;

trans-5-(1E-propenyl)-2-(4'-chloro-3'-fluoro-4-biphenylyl)-1,3-dioxane;

trans-5-(1E-pentenyl)-2-(4'-chloro-3'-fluoro-4-biphenylyl)-1,3-dioxane;

trans-5-(1E-propenyl)-2-(3',4'-dichloro-4-biphenylyl)-1,3-dioxane;

trans-5-[trans-4-vinylcyclohexyl]-2-(3,4-difluorophenyl)-1,3-dioxane;

trans-5-[trans-4-(1E-propenyl)cyclohexyl]-2-(3,4-difluorophenyl)-1,3-dioxane;

trans-5-[trans-4-(1E-pentenyl)cyclohexyl]-2-(3,4-difluorophenyl)-1,3-dioxane;

trans-5-[trans-4-vinylcyclohexyl]-2-(4-chlorophenyl)-1,3-dioxane;

trans-5-[trans-4-(1E-propenyl)cyclohexyl]-2-(4-chlorophenyl)-1,3-dioxane;

trans-5-[trans-4-(1E-pentenyl)cyclohexyl]-2-(4-chlorophenyl)-1,3-dioxane;

trans-5-[trans-4-vinylcyclohexyl]-2-(4-chloro-3-fluorophenyl)-1,3-dioxane;

trans-5-[trans-4-(1E-propenyl)cyclohexyl]-2-(4-chloro-3-fluorophenyl)-1,3-dioxane;

trans-5-[trans-4-(1E-propenyl)cyclohexyl]-2-(3,4-dichlorophenyl)-1,3-dioxane.

EXAMPLE 2 a) A solution of 7.47 g of 1,4-dioxa-8-spiro[4.5]decanone in 40 ml of tetrahydrofuran was added dropwise at 5° C. within 30 minutes to a Grignard reagent solution prepared from 1.21 g of magnesium, 9.45 g of 1-bromo-3,4-difluorobenzene and 35 ml of tetrahydrofuran. The reaction mixture was stirred at room temperature for a further 3 hours and at the boiling temperature for 2 hours. The red-brown solution was diluted with 80 ml of diethyl ether, washed once with 60 ml of 1N ammonium chloride solution and with three 40 ml portions of water, dried over sodium sulphate and concentrated. There were obtained 11.20 g of solid 8-(3,4-difluorophenyl)-1,4-dioxa-8-spiro[4.5]decanol.

b) A mixture of 11.2 g of 8-(3,4-difluorophenyl)-1,4-dioxa-8-spiro[4.5]decanol, 300 ml of toluene, 2.4 ml of ethylene glycol and 2.1 g of Amberlyst ® 15 (strongly acidic ion exchanger, Fluka AG) was boiled for 3.5 hours on a Dean-Stark trap. Then, the reaction mixture was neutralized with 1 ml of triethylamine, stirred for 5 minutes and the ion exchanger was filtered off. The filtrate was washed with two 40 ml portions of water, dried over sodium sulphate and concentrated. Chromatographic purification of the residue on 70 g of silica gel with hexane/ethyl acetate (vol. 9:1) gave 6.44 g of solid 8-(3,4-difluorophenyl)-1,4-dioxa-7-spiro[4.5]decene.

c) A solution of 6.44 g of 8-(3,4-difluorophenyl)-1,4-dioxa-7-spiro[4.5]decene, 1 ml of triethylamine and 125 ml of toluene/acetone (vol. 4:1) was hydrogenated with 1 g of palladium/carbon (10%) at room temperature and normal pressure until the hydrogen uptake came to a standstill. The catalyst was filtered off from the reaction mixture and the filtrate was concentrated. There were obtained 6.30 g of colourless, solid 8-(3,4-difluorophenyl)-1,4-dioxaspiro[4.5]decane.

d) A mixture of 6.30 g of 8-(3,4-difluorophenyl)-1,4-dioxaspiro[4.5]decane, 60 ml of toluene and 40 ml of formic acid was stirred for 18 hours. The formic acid phase was separated and extracted twice with 30 ml of toluene each time. The combined toluene phase was washed neutral with water, dried over sodium sulphate and concentrated. There were obtained 5.00 g of 4-(3,4-difluorophenyl)cyclohexanone as a colourless oil.

e) 4.1 g of potassium t-butylate were added in an inert gas atmosphere to a suspension of 12.2 g of dry methoxymethyltriphenylphosphonium chloride in 125 ml of t-butyl methyl ether and the orange-red suspension was stirred for 30 minutes. A solution of 5.00 g of 4-(3,4- difluorophenyl)cyclohexanone in 75 ml of t-butyl methyl ether was added dropwise at 0°–5° C. within 1 hour. The reaction mixture was stirred at 0°–5° C. for a further 1 hour and at room temperature for 2.5 hours and then treated with 50 ml of saturated sodium hydrogen carbonate solution. The organic phase was washed with water and concentrated. The residue was taken up in 200 ml of hexane and 100 ml of 80 percent aqueous methanol. The hexane phase was washed with two 40 ml portions of 80 percent methanol, dried over sodium sulphate and concentrated. There were obtained 5.6 g of 1,2-difluoro-4-[4-(methoxymethylidene)cyclohexyl]benzene.

f) A solution of 5.6 g of 1,2-difluoro-4-[4-(methoxymethylidene)cyclohexyl]benzene in 125 ml of tetrahydrofuran/2N hydrochloric acid (vol. 4:1) was heated to 90° C. for 1.25 hours. The reaction mixture was subsequently poured on to ice-water and extracted with diethyl ether. The ether phase was washed neutral with 50 ml of semi-saturated sodium hydrogen carbonate solution and with two 50 ml portions of water, dried over sodium sulphate and concentrated. A solution of the resulting crude trans/cis mixture (5.1 g) in 25 ml of methanol was added dropwise in an inert gas atmosphere at 0°–3° C. within 5 minutes to 70 ml of 0.1N methanolic potassium hydroxide solution. The reaction mixture was stirred at 0° C. for 1 hour, then poured on to 200 ml of ice-water and extracted with diethyl ether. The ether phases were washed neutral with water, dried over sodium sulphate and concentrated. There were obtained 4.8 g of trans-4-(3,4-difluorophenyl)cyclohexanecarboxaldehyde (cis content 5.7%).

The following compounds can be prepared in an analogous manner:
trans-4-(4-chlorophenyl)cyclohexanecarboxaldehyde,
trans-4-(4-chloro-3-fluorophenyl)cyclohexanecarboxaldehyde,
trans-4-(3,4-difluorophenyl)cyclohexanecarboxaldehyde.

EXAMPLE 3 a) A Grignard reagent solution prepared from 1.0 g of magnesium, 7.6 g of 1-bromo-3,4-difluorobenzene and 75 ml of tetrahydrofuran was added dropwise to a mixture of 9.0 g of 2-(p-iodophenyl)dioxolane, 100 ml of tetrahydrofuran, 0.025 g of palladium(II) chloride and 0.16 g of 1,3-bis(triphenylphosphino)propane. The reaction mixture was heated to boiling for 3 days and, after cooling, extracted with 200 ml of diethyl ether and 120 ml of 0.5N ammonium chloride solution. The organic phase was washed with three 80 ml portions of water, dried over sodium sulphate and concentrated. Chromatographic purification of the residue on silica gel with hexane/ethyl acetate (vol. 9:1) gave pure 2-(3',4'-difluoro-4-biphenylyl)dioxolane; m.p. 89°–91° C.

b) A mixture of 5.4 g of 2-(3',4'-difluoro-4-biphenylyl)dioxolane; 100 ml of toluene and 20 ml of formic acid was stirred for 16 hours. The formic acid phase was separated and the toluene phase was washed neutral with two 50 ml portions of saturated sodium hydrogen carbonate solution and three 75 ml portions of water, dried over sodium sulphate and concentrated. There were obtained 4.3 g of p-(3,4-difluorophenyl)benzaldehyde.

The following compounds can be prepared in an analogous manner:
p-(4-chlorophenyl)benzaldehyde,
p-(4-chloro-3-fluorophenyl)benzaldehyde,
p-(3,4-difluorophenyl)benzaldehyde.

EXAMPLE 4 a) A mixture of 33.3 g of 4-(1E-pentenyl)cyclohexanone (prepared in accordance with EP-A-168683), 42 ml of ethyl cyanoacetate, 300 ml of toluene and 2.9 g of piperidinium acetate is boiled for 1.5 hours on a water separator. After cooling the reaction mixture is washed with three 50 ml portions of water, dried over sodium sulphate and concentrated. Chromatographic purification of the residue on 750 g of silica gel with hexane/ethyl acetate (vol. 19:1) gives ethyl cyano-[4-(1E-pentenyl)cyclohexylidene]-acetate.

b) A solution of 46.0 g of ethyl cyano-[4-(1E-pentenyl)cyclohexylidene]acetate in 120 ml of ethanol is added dropwise at 5°–10° C. within 40 minutes to a mixture of 6.7 g of sodium borohydride and 120 ml of ethanol. The reaction mixture is stirred at 5° C. for 45 minutes, then diluted with 750 ml of water and extracted with three 250 ml portions of diethyl ether. The extract is washed neutral with water, dried over sodium sulphate and concentrated. There is obtained crude ethyl cyano-[trans-4-(1E-pentenyl)cyclohexyl]acetate (cis content <20%).

c) A mixture of 36.9 g of potassium hydroxide, 250 ml of water, 250 ml of ethanol and 37.2 g of ethyl cyano-[trans-4-(1E-pentenyl)cyclohexyl]acetate is heated to boiling for 3 days while stirring. After cooling the reaction mixture is diluted with 500 ml of water and washed with two 200 ml portions of diethyl ether. 220 ml of 10 percent (v/v) sulphuric acid are added dropwise to the aqueous phase. The precipitated product is extracted with three 200 ml portions of diethyl ether. The extract is washed with two 50 ml portions of water, dried over sodium sulphate, filtered and concentrated. Repeated recrystallization from benzene/hexane (vol. 1:1) gives pure [trans-4-(1E-pentenyl)cyclohexyl]malonic acid.

d) A solution of 28.6 g of [trans-4-(1E-pentenyl)cyclohexyl]malonic acid in 150 ml of absolute diethyl ether is added dropwise in an inert gas atmosphere within 1 hr. to a suspension of 8.6 g of lithium aluminium hydride in 250 ml of absolute diethyl ether in such a manner that the mixture does not boil too strongly. The mixture is heated to boiling for a further 4 hours and then there are cautiously added dropwise thereto 15 ml of ice-cold water and thereafter 250 ml of 25 percent (v/v) sulphuric acid until the aqueous phase thickens to a grey sludge. The ether phase is decanted and the residue is extracted with four 200 ml portions of diethyl ether. The combined ether phase is washed once with 25 ml of 25 percent sulphuric acid, with two 25 ml portions of saturated sodium hydrogen carbonate solution and with two 25 ml portions of saturated sodium chloride solution, then dried over sodium sulphate and concentrated. Fractional distillation of the residue in a high vacuum gives pure 2-[trans-4-(1E-pentenyl)cyclohexyl]-1,3-propanediol.

The following compounds can be prepared in an analogous manner:
2-[trans-4-vinylcyclohexyl]-1,3-propanediol,
2-[trans-4-(1E-propenyl)cyclohexyl]-1,3-propanediol,
2-[trans-4-(1E-butenyl)cyclohexyl]-1,3-propanediol.

EXAMPLE 5

Binary mixtures were prepared in order to investigate the properties of the compounds of formula I in mixtures. The threshold potential and the response times were measured in a TN cell (low bias tilt) having a plate separation of 8 μm; the 2.5-fold value of the threshold potential was selected as the operating voltage.

Mixture A 80 mol % of 4-(2E-butenyloxy)-1-(trans-4-propylcyclohexyl)benzene, 20 mol % of trans-5-(1E-propenyl)-2-[trans-4-(3,4-difluorophenyl)cyclohexyl]-1,3-dioxane;

m.p. (C-N) 22° C., cl.p. (N-I) 60.9° C., $k_{33}/k_{11}$ (50.9° C.)=1.21 $\Delta\epsilon$ (22° C.)=3.314, $\Delta\epsilon$ (50.9° C.)=2.378, $\Delta n$=(50.9° C.)=0.085; $\eta$ (22° C.)=15.8 cP; $\eta$ (50.9° C.)=6.1 cP, $\gamma_1$(50.9° C.)=24.5 cP; $V_{10}$(22° C.)=2.6 V, $V_{10}$ (50.9° C.)=2.0 V; $t_{on}$ (22° C.)=11 ms, $t_{on}$ (50.9° C.)=6.2 ms, $t_{off}$(22° C.)=20 ms, $t_{off}$(50.9° C.)=11 ms.

Properties of pure 4-(2E-butenyloxy)-1-(trans-4-propylcyclohexyl)benzene: m.p. (C-N) 42.4° C., cl.p. (N-I) 57.5° C.; $k_{33}/k_{11}$ (47.5° C.)=1.16, $\Delta\epsilon$ (47.5° C.)=-0.268, $\Delta n$ (47.5° C.)=0.089; $\eta$ (22° C.)=13.5 cP, $\eta$ (47.5° C.)=4.7 cP, $\gamma_1$ (22° C.)=86 cP, $\gamma_1$ (47.5° C.)=25 cP.

Mixture B 90 wt. % of 4-(trans-4-pentylcyclohexyl)benzonitrile,
10 wt. % of trans-5-(1E-butenyl)-2-[trans-4-(3,4-difluorophenyl)cyclohexyl]-1,3-dioxane;

cl.p. (N-I) 54.5° C., $V_{10}$=1.32 V, $t_{on}$=28 ms, $t_{off}$=46 ms, $\Delta n$=0.120.

Mixture C 80 wt. % of 4-(trans-4-pentylcyclohexyl)benzonitrile,
20 wt. % of trans-5-(1E-butenyl)-2-[trans-4-(3,4-difluorophenyl)cyclohexyl]-1,3-dioxane;

cl.p. (N-I) 54.6° C., $V_{10}$=1.24 V, $t_{on}$=33 ms, $t_{off}$=53 ms, $\Delta n$=0.112.

Mixture D 90 wt. % of 4-(trans-4-pentylcyclohexyl)benzonitrile,
10 wt. % of trans-5-(1E-propenyl)-2-[trans-4-(3,4-difluorophenyl)cyclohexyl]-1,3-dioxane;

cl.p. (N-I) 54.9° C., $V_{10}$=1.39 V, $t_{on}$=27 ms, $t_{off}$=47 ms, $\Delta n$=0.118.

Properties of pure 4-(trans-4-pentylcyclohexyl)benzonitrile: cl.p. (N-I) 54.6° C., $V_{10}$=1.62 V, $t_{on}$=30 ms, $t_{off}$=42 ms, $\Delta n$=0.120.

We claim:

1. A compound of the formula

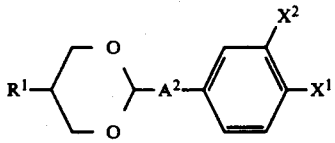

wherein $A^2$ is 1,4-phenylene or trans-1,4-cyclohexylene; $X^1$ is fluorine or chlorine; $X^2$ is fluorine, or when $X^1$ is chlorine, $X^2$ also can be hydrogen or chlorine; and $R^1$ is 1E-alkenyl with 2 to 12 carbon atoms.

2. The compound according to claim 1, wherein $R^1$ is straight-chain, 1E-alkenyl.

3. The compound according to claim 1, wherein $R^1$ is 1E-alkenyl with 2 to 7 carbon atoms.

4. The compound according to claim 3, wherein $R^1$ is 1E-alkenyl with 2 to 5 carbon atoms.

5. The compound according to claim 1, wherein each of $X^1$ and $X^2$ is fluorine.

6. The compound according to claim 1, wherein $X^1$ is chlorine and $X^2$ is hydrogen.

7. A liquid crystalline mixture having at least two components, wherein at least one of said components is a compound of the formula

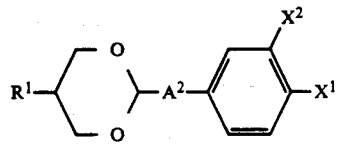

wherein $A^2$ is 1,4-phenylene or trans-1,4-cyclohexylene; $X^1$ is fluorine or chlorine; $X^2$ is fluorine, or when $X^1$ is chlorine, $X^2$ also can be hydrogen or chlorine; and $R^1$ is 1E-alkenyl with 2 to 12 carbon atoms.

8. The liquid crystalline mixture according to claim 7, wherein the amount of compound I is of about 1 to about 50% by weight of the mixture.

9. The liquid crystalline mixture according to claim 8, wherein the amount of compound I is about 5 to about 30% by weight of the mixture.

10. An electro-optical cell comprising:
a. two plate means;
b. liquid crystal means disposed between the two plate means and including a compound of the formula

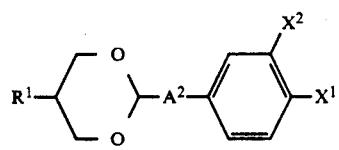

wherein $A^2$ is 1,4-phenylene or trans-1,4-cyclohexylene; $X^1$ is fluorine or chlorine; $X^2$ is fluorine, or when $X^1$ is chlorine, $X^2$ also can be hydrogen or chlorine; and $R^1$ is 1E-alkenyl with 2 to 12 carbon atoms; and
c. means for applying an electric potential to said plate means.

* * * * *